United States Patent [19]

Mendes et al.

[11] Patent Number: 5,580,353
[45] Date of Patent: Dec. 3, 1996

[54] PROSTHETIC PATELLA IMPLANT OF THE KNEE JOINT

[76] Inventors: David Mendes; Ruth Beer, both of 8 Keller, Haifa, Israel

[21] Appl. No.: 375,085

[22] Filed: Jan. 19, 1995

[30] Foreign Application Priority Data

Apr. 19, 1994 [IL] Israel .......................................... 109344

[51] Int. Cl.⁶ ........................................................ A61F 2/38
[52] U.S. Cl. ................................................ 623/20; 623/18
[58] Field of Search ........................................... 623/18, 20

[56] References Cited

U.S. PATENT DOCUMENTS

| | | | |
|---|---|---|---|
| 4,158,894 | 6/1979 | Worrell | 623/20 |
| 4,944,756 | 7/1990 | Kenna | 623/20 |
| 4,979,957 | 12/1990 | Hodorek | 623/20 |
| 5,019,104 | 5/1991 | Whiteside et al. | 623/20 |
| 5,236,462 | 8/1993 | Mikhail | 623/20 |
| 5,246,460 | 9/1993 | Goodfellow et al. | 623/20 |

*Primary Examiner*—David Isabella
*Attorney, Agent, or Firm*—Mark M. Friedman

[57] ABSTRACT

A patella (knee cap) implant for fixation to the remaining portion of a natural patella and for sliding over a femoral articulating member, the implant including an upper surface, typically convex, for sliding over the femoral articulating member, typically a groove, and a concave undersurface for fixation to the remaining portion of the natural patella. Also provided is a tool for preparing the natural patella to accept a patella implant and a method for surgically fixing the patella implant.

32 Claims, 2 Drawing Sheets

PRIOR ART

PROSTHETIC PATELLA IMPLANT OF THE KNEE JOINT

FIELD AND BACKGROUND OF THE INVENTION

The present invention relates to surgical implants or prosthetics and, more particularly, to a design for an artificial patella, or knee cap, and methods and tools for its installation.

Joint replacement is becoming increasingly widespread. One of the most widely practiced joint replacement involves the knee joint. In many cases, the replacement of the knee joint with a prosthetic also involves the replacement of a portion of the patella with a prosthetic.

Partial replacement of the patella is widely used in the surgical replacement of a damaged portion of the knee joint. However, it is known that, in a significant percentage of the cases, the patella implant typically fails after five to fifteen years. One of the typically occurring failures is near or at the periphery of the circular or elliptical patella implant, where the thickness of the patella implant material, typically high molecular weight high density polyethylene (HDPE), is at its smallest. A failing patella could lead to significant pain in the patient and typically requires a second operation to replace the failed patella implant.

There is thus a widely recognized need for, and it would be highly advantageous to have, a patella implant which will be more durable than those currently known and which will be significantly less prone to damage due to insufficient thickness, typically about its periphery.

SUMMARY OF THE INVENTION

According to the present invention there is provided a patella implant for fixation to the remaining portion of a natural patella and for sliding over a femoral articulating member, comprising: (a) an upper surface for sliding over the femoral articulating member; and (b) a substantially concave undersurface for fixation to the remaining portion of the natural patella.

Also according to the present invention, there is provided a reamer for use in preparing a natural patella to accept a patella implant having a substantially concave undersurface, comprising a concave rotatable reaming member, the concavity of the rotatable member being substantially equal to the concavity of the undersurface.

Further according to the present invention there is provided a method of repairing a natural patella, comprising: (a) preparing the natural patella by removing a portion thereof so as to leave a convex remaining portion; (b) fixing a patella implant onto the convex remaining portion of the natural patella, the patella implant having an upper surface for sliding over the femoral articulating member and a substantially concave undersurface for fixation to the convex remaining portion of the natural patella.

According to further features in preferred embodiments of the invention described below, the patella implant has a minimum thickness, typically at its periphery, of not less than about 6 or 8 mm.

The present invention relates to a special design for surgical replacement of part of the natural patella (knee cap) with a prosthetic part. The invention has been found particularly useful for patella replacement combined with replacement of all articulating parts of the knee joint but is also useful for replacement of the patella only.

An object of the present invention is to provide a design and a surgical method (including a surgical tool) for fixing the patella implant to the remaining portion of the natural patella which will enhance the strength and durability of the patella implant in vivo.

According to the present invention there is provided a design which will enable the manufacture of a HDPE patella implant with an overall thickness of not less than about 8 mm. This thickness is considered in the scientific literature as an optimal thickness for a high molecular weight high density polyethylene (HDPE) patella implant for use in an average person weighing 60–70 kg, for preventing high stresses within the material. Smaller thicknesses are to be used in smaller patients.

The use of the augmented minimum thickness eliminates one of the main causes of failure of patella implants and enhances the durability of the implant.

A patella implant according to the present invention is disc-shaped, typically either circular or elliptical, and has a typical diameter of about 25 to about 40 mm which roughly matches the diameter of the bony patella. The disc-like implant is characterized in that it has a concave undersurface. The implant also has an upper surface which may have any suitable shape, including, but not limited to, concave and flat, but preferably, is substantially convex. In the case of a convex upper surface, the convexity may, but need not, conform to the concavity of the undersurface.

To provide the required optimal thickness of the patella implant, the natural patella is cut, reamed and trimmed in such a manner as to remove a total of up to about 8 mm or more from the natural bone and cartilage to leave a convex shape which complements the concave shape of the undersurface of the patella implant.

The concave undersurface of the patella implant fits the appropriately reamed remaining portion of the natural patella. The upper surface articulates with the articulating femoral member, typically a groove, and is shaped to fit the corresponding articulating portion of the femoral component of the total knee implant. When the articulating femoral member is a groove, the upper surface of the implant is typically substantially convex. Where the upper surface is convex the convexity of the upper surface and the concavity of the undersurface of a patella implant according to the present invention do not necessarily conform to each other and may be independently varied to accommodate the specific design of the femoral groove, or its equivalent, and the convexity of the prepared natural patella.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a patella implant which can be used in the surgical repair of knee joints.

The principles and operation of a patella implant according to the present invention may be better understood with reference to the drawings and the accompanying description.

Figure 1:
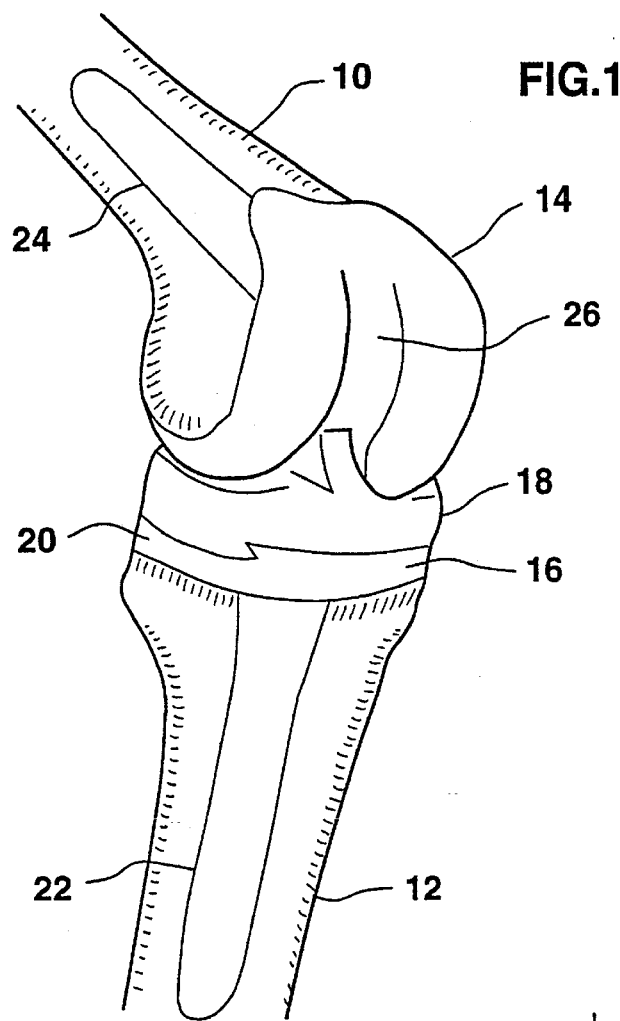
FIG. 1 is a perspective view of a typically artificial knee joint.

Referring now to the drawings, FIG. 1 illustrates a typical knee joint prosthetic. The knee joint is formed between the lower end of the femur 10 and the upper end of the tibia 12. In a total knee replacement, the lower end of femur 10 is replaced with a femoral prosthetic component 14 while the upper end of tibia 12 is replaced with a tibial prosthetic component 16.

Tibial prosthetic component 16 is typically made up of a plastic upper plate 18 and a metal back 20. A tibial anchorage stem 22 connected to metal plate 18 is typically used to anchor tibial prosthetic component 16 into tibia 12.

Femoral prosthetic component 14 is typically made of metal and is anchored into femur 10 with a femoral anchorage stem 24. The face of femoral prosthetic component 14 which contacts tibial prosthetic component 16 is typically shaped to mimic the natural knee to include a groove 26. It is on groove 26, or its equivalent, that the patella slides, as can be best be seen in FIG. 2.

Figure 2:
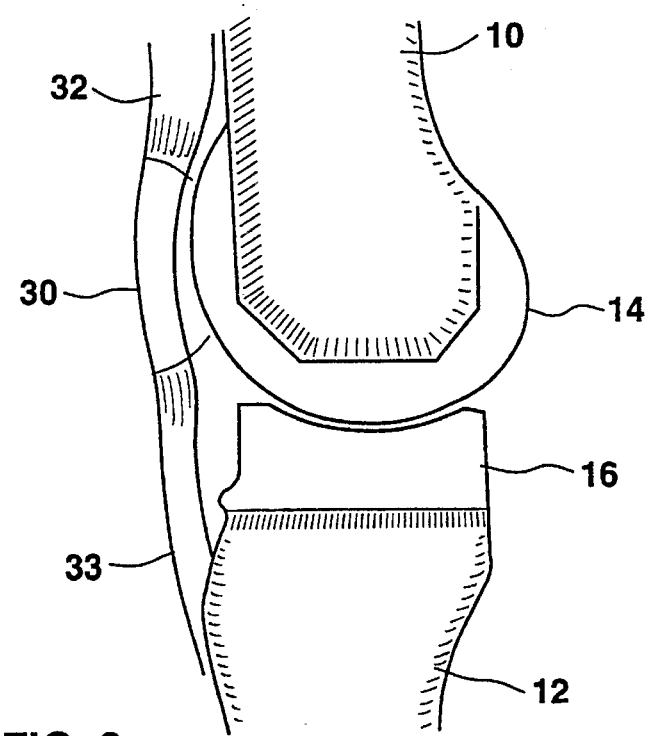
FIG. 2 is a side view of an artificial knee joint as in FIG. 1 showing the patella, quadriceps tendon and patella tendon.

FIG. 2 illustrates a total knee implant including the replacement of the articulating portion (the portion facing the knee) of the patella. As FIG. 2 illustrates, the patella (knee cap) 30 is a disc-shaped member which is connected to the quadriceps tendon 32 and to the patella tendon 33 and is slidable over the lower end of femur 10. The portion of patella 30 facing the knee (the patella implant) is typically, but not necessarily, convex and is dimensioned to slidably engage the corresponding portion of femoral prosthetic component 14, typically groove 26 (FIG. 1). The portion of patella 30 away from the knee (the remaining natural patella) is connected to quadriceps tendon 32 and patella tendon 33. Quadriceps tendon 32 is connected to the quadriceps muscle which is, in turn, attached to femur 10. Patella tendon 33 is connected to tibia 12. In this way patella 30 slides over the knee joint during flexion and extension of the joint. The presence of patella 30 facilitates the sliding of quadriceps tendon 32 and further enhances its mechanical efficiency.

To surgically repair a damaged patella what is done is to remove a portion of the articulating surface (the surface facing the knee joint) of the natural patella leaving the connection between the natural patella and the muscle intact. The removal is typically effected using a vibrating saw or similar instrument.

Once a portion of the patella has been removed, a prosthetic, or implant, may be fixed to the remaining portion of the natural patella by some suitable means. The implant is shaped to slidably fit within the groove, of equivalent, of the corresponding natural or prosthetic lower end of the femur, depending on whether the natural lower femur is to remain or be replaced, respectively. Attachment of the implant to the natural patella may be effected with adhesives, cements or other bonding materials and/or through use of pegs, as described in more detail below.

Figure 4:
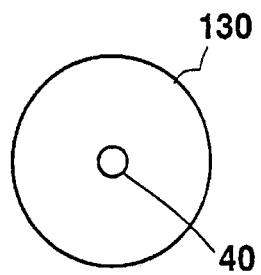
FIG. 4 is a back view of the patella implant of FIG. 3.
Figure 3:
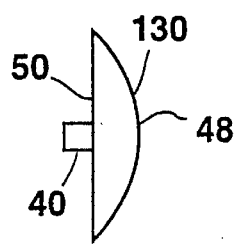
FIG. 3 is a cross sectional view of a conventional prior art patella implant.
Figure 5:
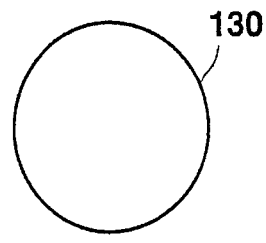
FIG. 5 is a front view of the patella implant of FIG. 3.
Figure 7:
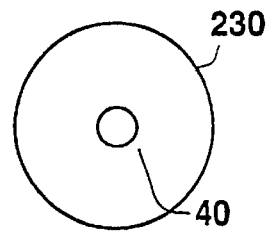
FIG. 7 is a back view of the patella implant of FIG. 6.
Figure 6:
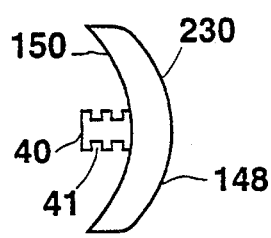
FIG. 6 is a cross sectional view of one embodiment of a patella implant according to the present invention.
Figure 8:
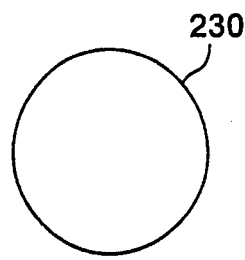
FIG. 8 is a front view of the patella implant of FIG. 6.
Figure 10:
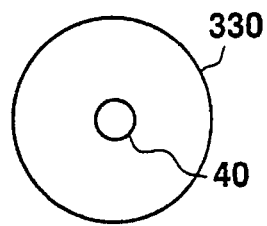
FIG. 10 is a back view of the patella implant of FIG. 9.
Figure 9:
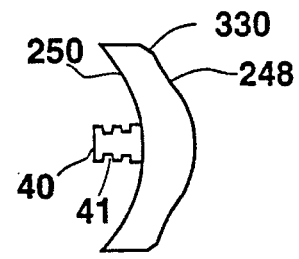
FIG. 9 is a cross sectional view of another embodiment of a patella implant according to the present invention.
Figure 11:
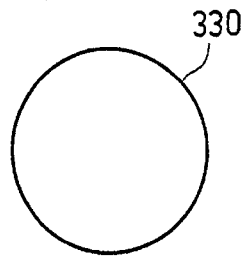
FIG. 11 is a front view of the patella implant of FIG. 9.
Figure 12:
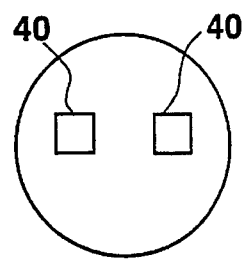
FIG. 12 is a back view of a patella implant showing a pair of fixation members.
Figure 13:
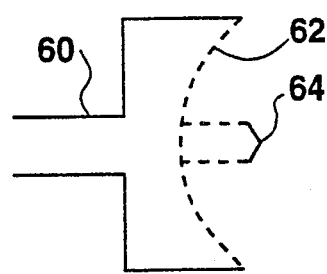
FIG. 13 is a back view of a patella implant showing four fixation members.

A typical conventional patella implant is shown in side, back and front views in FIGS. 3, 4 and 5, respectively. Patella implants are typically circular in back and front views (FIGS. 4 and 5) but may also be elliptical, (as can be seen in FIGS. 10 and 11) or may assume other shapes. Furthermore, patella implants typically include one or more protrusions, or pegs, 40 which are inserted into the natural patella and help firmly fix, typically with the addition of suitable adhesives, cements or other bonding materials, the implant and the remaining portion of the natural patella. Protrusions 40 may be integrally formed with the implant or may be connected to it in some suitable fashion, as by screwing, for example. The one or more protrusions 40 may be of various shapes, including, but not limited to square or rectangular (see FIGS. 12 and 13). Preferably, protrusions 40 are circular in cross-section, or cylindrical (FIGS. 3, 6 and 9). Most preferably, the implant includes a single central circular protrusion 40 (FIGS. 3, 6 and 9).

As can best be seen in the side view of FIG. 3, a conventional patella implant 130 includes a surface (hereinafter "upper surface") 48 of any suitable design, typically, but not necessarily, substantially convex, and a planar, i.e., flat, undersurface 50. To surgically install such an implant, the natural patella is cut in planar, or flat, fashion and the implant is bonded, or otherwise fixed, (with or without the help of one or more pegs 40) to the newly cut face of the natural patella.

The geometry of the conventional patella implant 130 is such that the periphery of implant 130 is very thin compared to its central portion. It has been determined that, because of this geometry, under the tremendous stresses to which the implant is exposed during normal use, failure of the implant frequently takes place mostly near and at the periphery. Failure typically results from wear, creep and fatigue cracks of the high molecular weight high density polyethylene from which the implant is made.

A patella implant according to the present invention overcomes these difficulties by providing a minimum thickness of the implant, including near and at its periphery, which is significantly larger than that available with the presently known implants described above. The increased thickness, particularly near and at the periphery, is accomplished by providing a substantially concave undersurface for fixation to the remaining portion of the natural patella.

Thus, with reference to FIGS. 6 and 9, a patella implant, 230 or 330, according to the present invention includes an upper surface, 148 or 248, which is typically, but not necessarily, substantially convex, for sliding over femoral groove 26, or its equivalent (FIG. 1). Upper surface, 148 or 248, can have any suitable shape designed to slidably engage groove 26 of femoral prosthetic component 14. Two illustrative examples of upper surface geometries, both substantially convex, are shown in FIGS. 6 and 9 wherein the substantially convex surface has a monotonically changing slope and a slope which features an inflection, respectively. The surface finish of the upper surface is preferably prepared in accordance with the conventional requirements of the Food and Drug Administration (FDA).

Patella implant, 230 or 330, is characterized in that it further includes a substantially concave undersurface, 150 or 250, for fixation to the remaining portion of the natural patella. The concavity of undersurface, 150 or 250, in contrast with the planar undersurface 50 of conventional patella implants (FIG. 3) makes it possible to have an implant with significantly larger minimum thickness, particularly around its periphery.

The diameter of the patella implant should approximately correspond to the size of the remaining natural patella. All portions of the patella implant, including the periphery, should preferably have thicknesses of not less than about 8 mm in the case of normal-sized patients and not less than about 6 mm in the case of small patients, where the implant material is high molecular weight high density polyethylene (HDPE). It will be readily appreciated that when different materials are used for the implant, including, but not limited to, other plastics, various metals, ceramics or composites, a different optimal minimum thickness will be appropriate.

As described above, the concave surface should preferably include one or more pegs 40 which are preferably either cylindrical or rectangular, but which can be any other geometrical shape. Pegs 40 may be of any suitable size, preferably at least 2 mm. Most preferably, pegs 40 should extend beyond the undersurface of the implant so that their distal end is substantially flush with the outer rim of the undersurface, typically about 6 mm. The diameter, or equivalent diameter, of pegs 40 should preferably be at least 5 mm, most preferably on the order of 10 mm.

Preferably, pegs 40 are formed with circumferential depressions 41 (FIGS. 6 and 9) which help improve the bonding and anchorage by providing enhanced friction and further providing space in which adhesives and the like can accumulate.

Pegs 40 are dimensioned to fit into holes prepared in the natural patella following the reaming of the bony patella during the preparation of the bony patella. Pegs 40 and the concave undersurface of the patella implant are prepared to fix to the natural patella either by means of suitable bonding materials, such as, for example, an acrylic cement, or by special materials fit for bone ingrowth, such as, for example, metallic or ceramic coatings.

According to a preferred embodiment of the present invention the patella implant is constructed of high molecular weight high density polyethylene, although other biocompatible materials, such as various metals, ceramics, plastics or composites, may be used. For convenience of the user the implants may be marketed in several overall diameters, for example, 25 mm with increments of 3–4 mm, and in several optional thicknesses, for example, 8 mm with increments of 1–2 mm. Of course, for small patients, implants with thicknesses of less than 8 mm will be available.

As will readily be appreciated, when an implant according to the present invention is made of a material other than HDPE, such as, for example, a metal, the recommended thickness may be different. However, the concepts of shape and anchorage described herein are the same.

The concave underside of the implant can have a single radius of curvature or can feature a flattened central portion. Other shapes are also possible and are intended to be included within the scope of the present invention. Other shapes may be used which will enhance the bonding of the implant to the natural patella. To further enhance the bonding and fixation of the implant to the bone, it may be desirable to use a number of pegs 40 of various shapes (for example, FIGS. 12 and 13).

To anchor pegs 40 in the natural patella, a single central or nearly central hole and/or one or more non-central holes are prepared in the remaining portion of the natural patella. Fixation of the prosthetic patella can be effected by means of a bonding material or other chemical, physical or biological adhesives and by biological reactions, such as bone ingrowth into the surface, preferably using the pegs which fit into their respective holes in the prepared bone surface. Alternatively or additionally, fixation may be effected by means of press fitting or other fixation techniques.

To prepare the natural patella bone to accept an implant according to the present invention, it is necessary to cut the bone so that it takes on the shape of the concave undersurface of the implant. The surgical preparation of the natural patella can be achieved using a special tool which cuts the bony patella to precisely the desired shape with minimal interference of its blood supply from the surrounding tissues.

Figure 14:
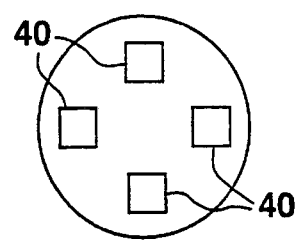
FIG. 14 is a side view of a reamer which may be used to prepare a natural patella for acceptance of a patella implant according to the present invention.

The special tool is a concave surgical reamer 60 (FIG. 14) which can be powered electrically, pneumatically, mechanically, manually, and the like. Reamer 60 can be used to remove an appropriate amount of bone in order to create a convex surface of cortical and/or cancellous bone of the bony patella which accurately fits the concave undersurface of a patella implant according to the present invention.

Reamer 60 includes a concave rotatable reaming member 62 whose concavity is substantially equal to the concavity of the patella implant undersurface. Preferably, reamer 60 further includes a bit 64 which protrudes from concave rotatable reaming member 62 and which is used to simultaneously drill a hole in the natural patella which will accommodate a single central peg extending from the undersurface of the implant.

While the invention has been described with respect to a limited number of embodiments, it will be appreciated that many variations, modifications and other applications of the invention may be made.

What is claimed is:

1. A patella implant adapted to structurally fit a remaining part of the natural patella with maximal reserving of healthy natural tissue and minimal wear of the implant, comprising:

(a) a substantially convex upper surface for sliding over a femoral articulating member;

(b) a substantially concave undersurface for fixation to a convexly sectioned natural patella, the distance between said upper surface and said undersurface having a value of at least about 8 mm; and (c) a circumferential facet, said facet having a height of at least about 8 mm.

2. A patella implant as in claim 1, wherein the implant is made of plastic.

3. A patella implant as in claim 1, wherein the implant is made of high molecular weight high density polyethylene.

4. A patella implant as in claim 1, wherein the implant is substantially circular in plan view.

5. A patella implant as in claim 1, wherein the implant is substantially elliptical in plan view.

6. A patella implant as in claim 1, wherein said undersurface features at least one protrusion for fixation to a convexly sectioned natural patella.

7. A patella implant as in claim 6, wherein said at least one protrusion is integrally formed with the implant.

8. A patella implant as in claim 6, wherein said at least one protrusion is connected to the implant.

9. A patella implant as in claim 6, wherein said at least one protrusion is substantially circular in cross-section.

10. A patella implant as in claim 6, wherein said at least one protrusion extends at least about 2 mm beyond said undersurface of the implant.

11. A patella implant as in claim 6, wherein said at least one protrusion has a diameter of at least about 5 mm.

12. A patella implant as in claim 4, wherein said upper surface and said undersurface feature a structure of a dome.

13. A patella implant as in claim 6, wherein said at least one protrusion features circumferential depressions.

14. A patella implant as in claim 1 adapted for specific geometries of said femoral articulating member and said convexly sectioned natural patella, wherein said distance between said upper surface and undersurface is variable and has a minimal value, and wherein said facet has a height of said minimal value.

15. A patella implant as in claim 14, wherein said upper surface and said undersurface feature a structure of a dome.

16. A patella implant as in claim 15, wherein said upper surface includes an inflection.

17. A patella implant adapted for light weight patients, the implant adapted to structurally fit a remaining part of the natural patella with maximal reserving of healthy natural tissue and minimal wear of the implant, comprising:

(a) a substantially convex upper surface for sliding over a femoral articulating member;

(b) a substantially concave undersurface for fixation to a convexly sectioned natural patella, the distance between said upper surface and said undersurface having a value of at least about 6 mm; and (c) a circumferential facet, said facet having a height of at least about 6 mm.

18. A patella implant as in claim 17, wherein the implant is made of plastic.

19. A patella implant as in claim 17, wherein the implant is made of high molecular weight high density polyethylene.

20. A patella implant as in claim 17, wherein the implant is substantially circular in plan view.

21. A patella implant as in claim 17, wherein the implant is substantially elliptical in plan view.

22. A patella implant as in claim 17, wherein said undersurface features at least one protrusion for fixation to a convexly sectioned natural patella.

23. A patella implant as in claim 22, wherein said at least one protrusion is integrally formed with the implant.

24. A patella implant as in claim 22, wherein said at least one protrusion is connected to the implant.

25. A patella implant as in claim 22, wherein said at least one protrusion is substantially circular in cross-section.

26. A patella implant as in claim 22, wherein stud at least one protrusion extends at least about 2 mm beyond said undersurface of the implant.

27. A patella implant as in claim 22, wherein said at least one protrusion has a diameter of at least about 5 mm.

28. A patella implant as in claim 20, wherein said upper surface and said undersurface feature a structure of a dome.

29. A patella implant as in claim 22, wherein said at least one protrusion features circumferential depressions.

30. A patella implant as in claim 17 adapted for specific geometries of said femoral articulating member and said convexly sectioned natural patella, wherein said distance between said upper surface and undersurface is variable and has a minimal value, and wherein said facet has a height of said minimal value.

31. A patella implant as in claim 30, wherein said upper surface and said undersurface feature a structure of a dome.

32. A patella implant as in claim 31, wherein said upper surface includes an inflection.

\* \* \* \* \*